(12) United States Patent
Asaba et al.

(10) Patent No.: US 6,249,751 B1
(45) Date of Patent: Jun. 19, 2001

(54) METHOD OF MEASURING GONIO-SPECTRAL REFLECTANCE FACTOR

(75) Inventors: Takao Asaba, Akashi; Koichi Kuwano, Osaka, both of (JP)

(73) Assignee: Nippon Paint Co., Ltd., Osaka (JP)

( * ) Notice: Subject to any disclaimer, the term of this patent is extended or adjusted under 35 U.S.C. 154(b) by 0 days.

(21) Appl. No.: 09/247,556

(22) Filed: Feb. 10, 1999

(30) Foreign Application Priority Data

Feb. 10, 1998 (JP) .................................................. 10-044471

(51) Int. Cl.[7] .............................. G06F 19/00; B05D 1/36
(52) U.S. Cl. ........................... 702/76; 702/72; 356/326; 356/402; 427/402; 427/409
(58) Field of Search .................................. 702/66, 72, 73, 702/76; 356/326, 328, 402, 407, 446; 427/380, 402, 409, 595, 597

(56) References Cited

U.S. PATENT DOCUMENTS

| | | | |
|---|---|---|---|
| 4,572,672 | * | 2/1986 | Orchard et al. ...................... 356/446 |
| 4,711,580 | * | 12/1987 | Venable ................................ 356/402 |
| 5,231,472 | * | 7/1993 | Marcus et al. ....................... 356/402 |
| 5,840,372 | * | 11/1998 | Rink et al. ........................... 427/409 |

* cited by examiner

Primary Examiner—Marc S. Hoff
Assistant Examiner—Bryan Bui
(74) Attorney, Agent, or Firm—Connolly Bove Lodge & Hutz

(57) ABSTRACT

The present invention is a method of measuring a gonio-spectral reflectance factor to establish a gonio-spectral reflectance factor database available for a personal computer by which a highly-fine realistic 3D computer graphics image can be formed. The method enables colorimetry in a reduced hours in fewer viewing directions compared to the conventional method by executing colorimetry in a plurality of viewing directions selected at random from all the directions that can be viewed by a goniospectrophotometer, said plurality of viewing directions being less than all the directions that can be viewed by the goniospectrophotometer.

12 Claims, 8 Drawing Sheets

(2 of 8 Drawing Sheet(s) Filed in Color)

METHOD OF MEASURING GONIO-SPECTRAL REFLECTANCE FACTOR

BACKGROUND OF THE INVENTION

1. Field of the Invention

The present invention relates to a method of measuring gonio-spectral reflectance factor. More particularly, it relates to a method of measuring, by a goniospectrophotometer, a gonio-spectral reflectance factor available for a database of colors of coating for rendering a three-dimensional computer graphics image.

2. Description of the Related Art

An analysis of a process in which an emitted light is reflected, transmitted, scattered and interfered on the surface and/or inside of an actual object and finally reaches to a receiving instrument or a receiving organ has been recently advanced. A technique of rendering a highly-fine realistic image in accordance with a gonio-spectral reflectance factor obtained by colorimetry of a coating plate is being advanced based on the approach for three-dimensional computer graphics using knowledge of these optics and colorimetry has been developed. This technique allows a color effect to be identified on a display when an object is coated with an actual coating and thus expected to contribute greatly to a design work, a work of developing a coating material, or the like. The term colorimetry means the measurement of a spectral reflectance factor for many wavelengths in a range of visible light wavelength.

The gonio-spectral reflectance factor has the parameters: a wavelength $\lambda$; the direction of incidence of the light on the specimen surface; and the direction of reflected light from the specimen surface. This gonio-spectral reflectance factor is typically obtained by the use of a goniospectrophotometer, changing a viewing angle at which the light reflected from the specimen is received and then measuring the spectral reflectance factor at each viewing angle.

In the implementation of the colorimetry, the conventional measuring method is that a viewing direction is regularly changed in such a manner as step by step change by constant inclination since it can easily cover every direction. That is, the viewing angles are set at predetermined intervals, and then parameters determining the viewing direction are changed by appropriate amount. The measurement is done sequentially with the viewing direction being changed step by step in many directions. For example, the reflected light generally undergoes the colorimetry at each step, while the viewing angle. which is defined as the angle formed between the reflection direction and specular direction in a plane of incidence, is sequentially changed step by step by a predetermined increment angle.

For forming the highly-fine realistic rendering image in accordance with actual colorimetry data in the three-dimensional computer graphics, the gonio-spectral reflectance factor measured in every viewing direction is required. That is, preferably, the reflectance factors of the lights having as many wavelengths as possible and as many directions as possible are gathered in order to reproduce a reflectance factor distribution of the actual object. Thus, for gathering the colorimetry data, the colorimetry is implemented in very many viewing directions, e.g., in about several thousands to about ten thousands viewing directions by using the goniospectrophotometer. However, the more an amount of data is, the more difficult the gathering of the actual colorimetry data is.

For instance, about two to three days are typically required for subjecting one specimen, i.e., one surface color of coating to the colorimetry. Much time and considerable efforts are consequently needed for subjecting many surface colors of coating to the colorimetry. This is a bottleneck in the creation of a database of colors of coating for which about tens of colors to about hundreds of colors are generally needed and it is also hard to supplement new data of surface color of coating into a database.

Moreover, the colorimetry data inevitably becomes large in scale and hence the database requires a large storage capacity of a computer. This is a disadvantage in ensuring a processing speed and a storage capacity of a computer when the data is processed by a personal computer.

Thus, the rendering is actually performed by the use of a limited number of colorimetry data by taking into account both of the processing speed and the storage capacity of a computer. In this case, some partial viewing directions such as about 1/10 to about 1/tens of all the possible viewing directions are selected from all the viewing directions that can be measured by the goniospectrophotometer (i.e. about several thousands to about ten thousands viewing directions) by selecting the viewing directions regularly at each of angles spaced at one or plural predetermined interval(s). However, it is difficult to obtain information on the spectral reflectance factor needed for the rendering with no sacrifice in the fineness and the reality. Even if the viewing angles are sparsely or densely spaced depending on a region to be measured, the number of the viewing directions cannot be greatly changed.

Therefore, a method of easily creating the colorimetry database is not yet provided.

Thus, an object of the present invention is to provide a method of measuring a gonio-spectral reflectance factor to establish a gonio-spectral reflectance factor database available for a personal computer by which a highly-fine realistic three-dimensional computer graphics image can be formed in a reduced hours of a colorimetry in fewer viewing directions compared to the conventional method.

SUMMARY OF THE INVENTION

The present invention provides a method of measuring gonio-spectral reflectance factor for use in a database of colors of coating for forming a three-dimensional computer graphics image, wherein a light reflected from a measured specimen is subjected to a colorimetry in plurality of viewing directions selected at random from all the directions that can be viewed by a goniospectrophotometer, said plurality of viewing directions being less than all the directions that can be viewed by a goniospectrophotometer.

According to a law of large numbers (a large sample theory), if n is large when an n-sized sample selected at random is taken from a population of observable numerical values, the statistical distribution characteristics of the sample is surely substantially equal to that of the population. A gonio-spectral reflectance factor distribution R ($\lambda$, P) is a function of a wavelength $\lambda$ and a viewing direction P. The viewing direction P typically includes about several thousands to about ten thousands directions. The gonio-spectral reflectance factor is obtained as a particular observed value $R_i$ viewed in a particular direction $P_i$ selected from these several thousands to ten thousands directions P. The gonio-spectral reflectance factor distribution R can be therefore considered to be the function which establishes the correspondence between a set $\{R_i\}$ of observed values of the gonio-spectral reflectance factor and a set $\{P_i\}$ of viewing directions.

All the viewing directions $P_i$ of about several thousands to about ten thousands directions (i=integers from 1 to about several thousands through about ten thousands)are regarded as one population for a certain measured wavelength. The n-sized sample $\{P_1, P_2, \ldots, P_n\}$ selected at random is made from this population and n is large, the distribution characteristics of the sample is considered to be approximate to the distribution characteristics of the population.

Meanwhile, the following fact is also being solved. That is, the recognition process includes an information processing in the cerebrum which plays an important part in a mechanism for recognizing an object image through a visual sensation of a human being. That is, the recognition by the human being of the object image through the visual sensation includes the decoding process for determining whether an external optical information input has a certain particular shape, texture or the like.

It may be also acceptable that all the physical optical information from the object is not used when the human being recognizes the object. In short, an observer discriminates the partial features, more particularly, the features which are recognizable to the observer, thereby forming a concept of the object.

The process of recognizing the reproduced object image by the human being comprises two processes: the process of physically forming the computer graphics image and the process of visually recognizing the computer graphics image by the human being. For forming the computer graphics image having the accuracy required for a task such as a design work and a presentation work, the extent of the accuracy in the colorimetry process should therefore be determined by taking into account an effect of all the processes on the image recognition by the human being. The present invention is based on the consideration that the number of points of measurement which has been needed in the colorimetry for the database of colors of coating can be greatly reduced without deteriorating the accuracy of the final image recognized by the human being.

In the present invention, the gonio-spectral reflectance factor therefore is subjected to the colorimetry in partial, e.g., 300–500 viewing directions selected at random from all the directions of the goniospectrophotometer, i.e., typically about several thousands to about ten thousands viewing directions. The colorimetry for the gonio-spectral reflectance factor is thereby accomplished in fewer viewing directions and it is thus possible to create the database of colors of coating capable of providing the colorimetry information required for forming the three-dimensional computer graphics image having the sufficient fineness and reality for practical use.

By the use of the thus formed database of colors of coating, it is also possible to form the three-dimensional computer graphics image in which the texture of a coating film such as a metallic texture, a silky texture and a pearlescent texture can be appeared.

BRIEF DESCRIPTION OF THE DRAWINGS

This application contains at least one drawing executed in color.

DETAILED DESCRIPTION OF THE PREFERRED EMBODIMENTS

Figure 4:
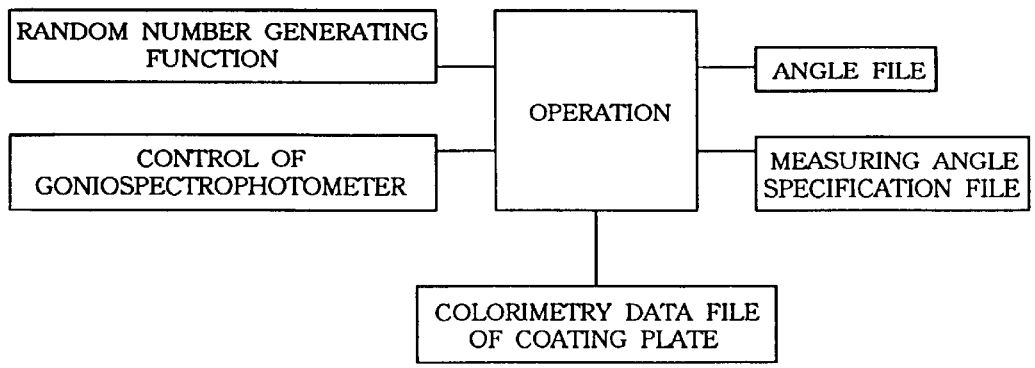
FIG. 4 is a diagram showing functions to be provided to a computer in the present invention.

A first embodiment provides a method of selecting at random partial plural viewing directions from all the directions that can be viewed by a goniospectrophotometer. In this method, a predetermined number of sets of measurable incident angles, viewing angles and tilt angles are selected at random from numerical values of angles generated at random in an angle file of a computer, and then these sets can preferably be stored in a measuring angle specification file in the computer. Preferably, the computer is provided with, at least, a function of generating random numbers, a function of controlling a measuring device of a goniospectrophotometer, an arithmetic function, means for storing the angle file, the measuring angle specification file and data to be used as a criterion obtained by measuring a coating plate, as shown in FIG. 4.

In general, a gonio-spectral reflectance factor R has total five degrees of freedom: a colorimetry wavelength $\lambda$; two angles $\theta_1$ and $\theta_2$ describing the direction of incidence of the light to the specimen surface; and two angles $\theta_3$ and $\theta_4$ describing the direction of reflection of the light from the specimen surface, where the angles $\theta_1$ through $\theta_4$ are determined in an appropriate rectangular coordinate system. The gonio-spectral reflectance factor R can be expressed as a multivariable function having five variables represented by $R(\lambda, \theta_1, \theta_2, \theta_3, \theta_4)$.

Figure 5:
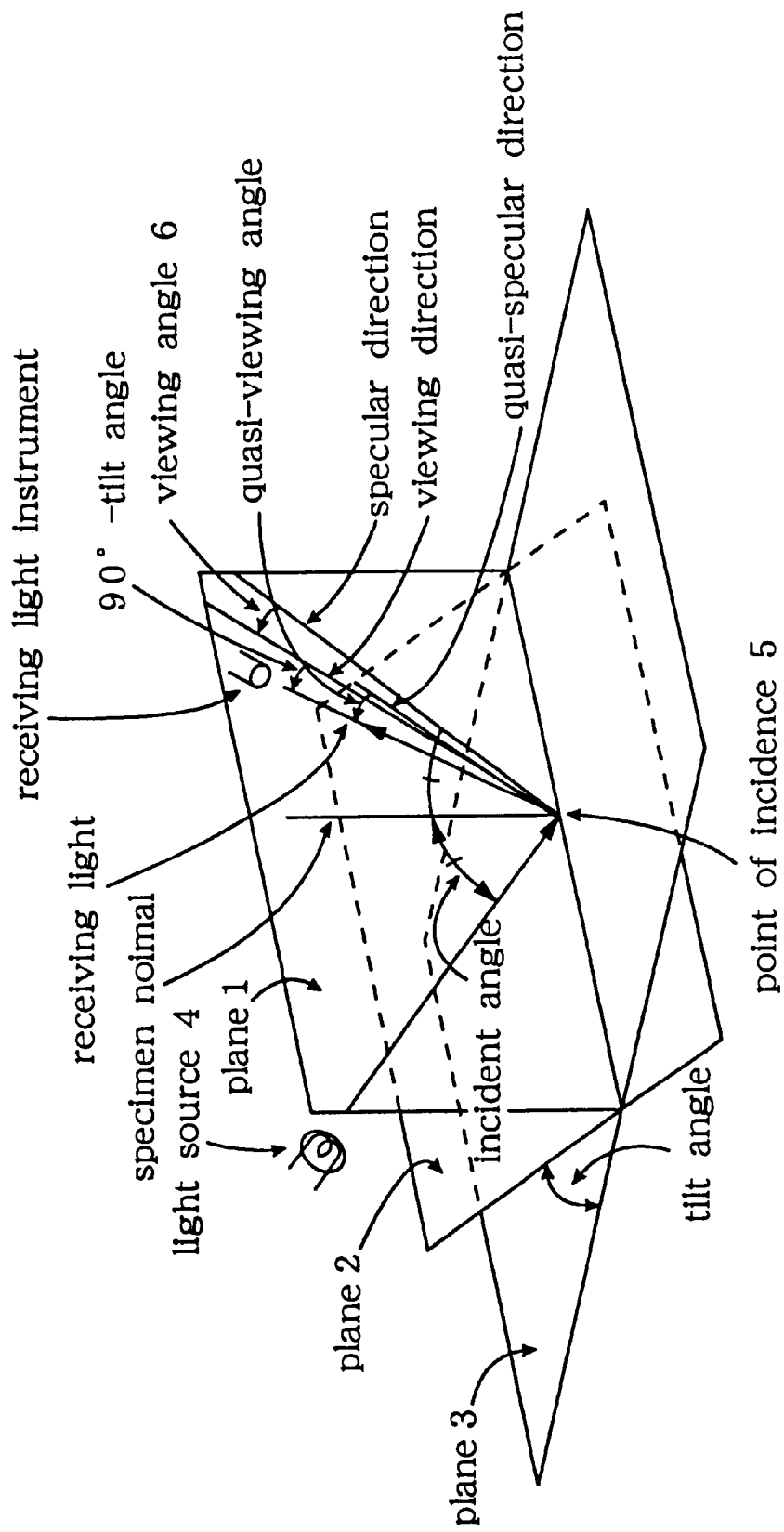
FIG. 5 is a conceptual illustration describing an incident angle, a viewing angle and a tilt angle.

The angle variables differ in expression depending on the coordinate systems. In the present invention, the angle variables are defined as the incident angle, the viewing angle and the tilt angle shown in FIG. 5. In FIG. 5, a plane 1 (plane of incidence) represents a plane including a normal line of the coating plate (plane of specimen) and an incident light. A plane 3 (plane of specimen) represents a plane of coating plate of specimen. The light from a light source 4 via a point of incidence is received by a receiving light instrument in a plane 2 (tilt plane) specified by the tilt angle represented by a viewing angle 6 and an angle of rotation from the plane 3. The method of selecting at random the lights reflected from the colorimetry specimen from all the viewing directions that can be measured by the goniospectrophotometer is therefore performed in the following manner.

The numerical values of the incident angles, viewing angles and tilt angles are first generated at random in the angle file in the computer. This can be executed by generating the uniform random numbers by the computer.

A format of the above angle file can be expressed in the following manner, for example.

<The number of measured wavelengths>
<Wavelength 1>|<Wavelength 2>| ... |<Wavelength x>
<Incident angle 1>|<Viewing angle 1>|<Tilt angle 1>
<Incident angle 2>|<Viewing angle 2>|<Tilt angle 2>
...
<Incident angle y>|<viewing angle y>|<Tilt angle y>

The measuring angles can be freely described in the above-mentioned file format. Unlike the prior art, it is therefore unnecessary to sequentially describe the measuring angles at constant intervals. Thus, desired angles can be appropriately described at random. The angles can be also freely described densely or sparsely in a desired angle region. In the angle file, the numerical values of angles generated at random is not need to be arranged in a particular order.

The numerical values of angles thus generated at random may include numerical values which cannot be actually measured by a particular measuring device due to a positional relationship between the receiving light instrument and the light source, e.g., the case where the receiving light instrument and the light source are located at the same position or the case where the incident light and the reflected light are completely horizontal.

In the present invention, a predetermined number n of sets of actually measurable incident angles, viewing angles and tilt angles are then selected at random from the numerical values of angles generated at random. However, the actually measurable angles generally differ depending on the measuring devices. In the present invention, a different file from the angle file is thus provided as the measuring angle specification file. A predetermined number n of numerical values of angles which can be measured by the employed measuring device are selected at random from the angle file, and then the selected values are stored in the measuring angle specification file in the computer. Accordingly, the angle file itself does not depend on a particular measuring device. As a result, the angle file is always applicable even if the measuring devices differ in the performance.

Preferably, n, i.e., the number of the viewing directions selected at random is in general from 300 to 500.

The measured wavelengths can be also described in the angle file or the measuring angle specification file. When the measuring device is controlled by the use of the computer, the numerical values of angles and wavelengths can be used as control data.

Preferably, the numerical values of angles in the measuring angle specification file are arranged in sequence convenient for the measuring device in order to effectively perform the measurement for the shortest time. In the present invention, preferably, the numerical values of angles stored in the measuring angle specification file are rearranged in sequence convenient for the measuring device before starting the measurement. The actual measurement is implemented in accordance with the rearranged angles.

In the angle file and the measuring angle specification file, a minimum value of a specification angle of the incident angle, the viewing angle and the tilt angle is not particularly limited. For example, a minimum value which can be expressed by a double-precision floating point can be taken as a minimum unit for the specification of angle. However, it is normally difficult for the actual measuring device to adjust the measuring angle to the angle specified by a minute unit. The practical measurement will be therefore implemented at the closest angle to the specified angle such as "57.5°" or "57°" when "57.49315°" is specified, for example.

By the use of the file format and the use of the angle file and the measuring angle specification file, desired angles can be appropriately specified and thus the measurement can be performed to the desired angles, unlike the prior art in which the measuring angles are sequentially specified at constant intervals. It is thus possible to minimize a measuring time and to realize flexibility of the measurement.

A second embodiment provides a method of selecting at random partial plural viewing directions from all the directions that can be viewed by the goniospectrophotometer. In this method, a gonio-spectral reflectance factor distribution of at least one coating plate to be a criterion is in advance determined, while a plurality of sets of numerical values of angles representing the viewing directions are generated at random, and a predictive gonio-spectral reflectance factor distribution is determined by the use of the reflectance factor specified by the gonio-spectral reflectance factor distribution in the viewing directions specified by said sets of numerical values of angles, whereby, trials are repeated until said predictive gonio-spectral reflectance factor distribution can be approximate to said original gonio-spectral reflectance factor distribution with a predetermined accuracy, then, a plurality of viewing directions by which said predictive distribution can be determined are selected. This process will be described below.

Figure 2:
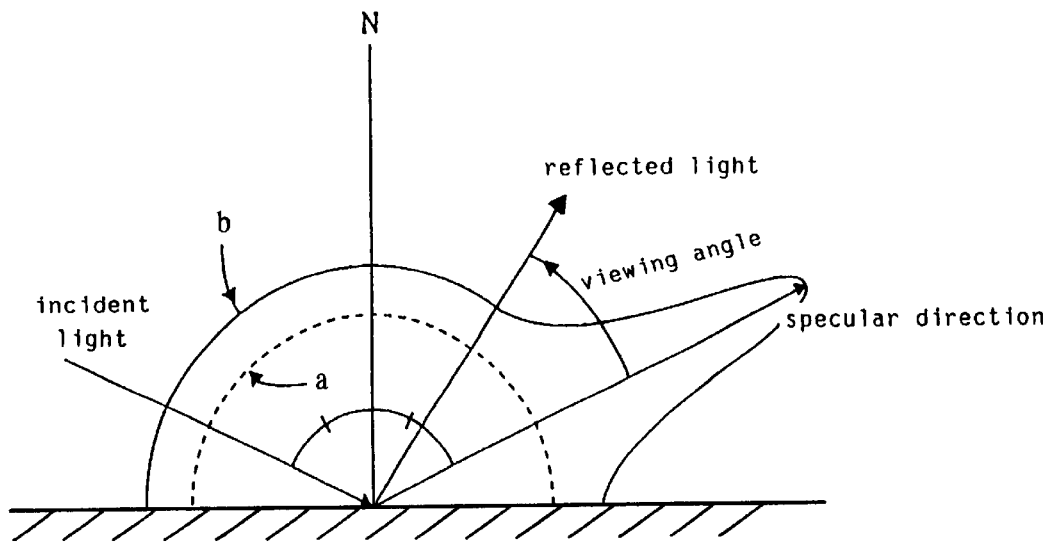
FIG. 2 is a conceptual illustration showing directional characteristics of a reflectance intensity of a light reflected from a specimen surface.
Figure 3:
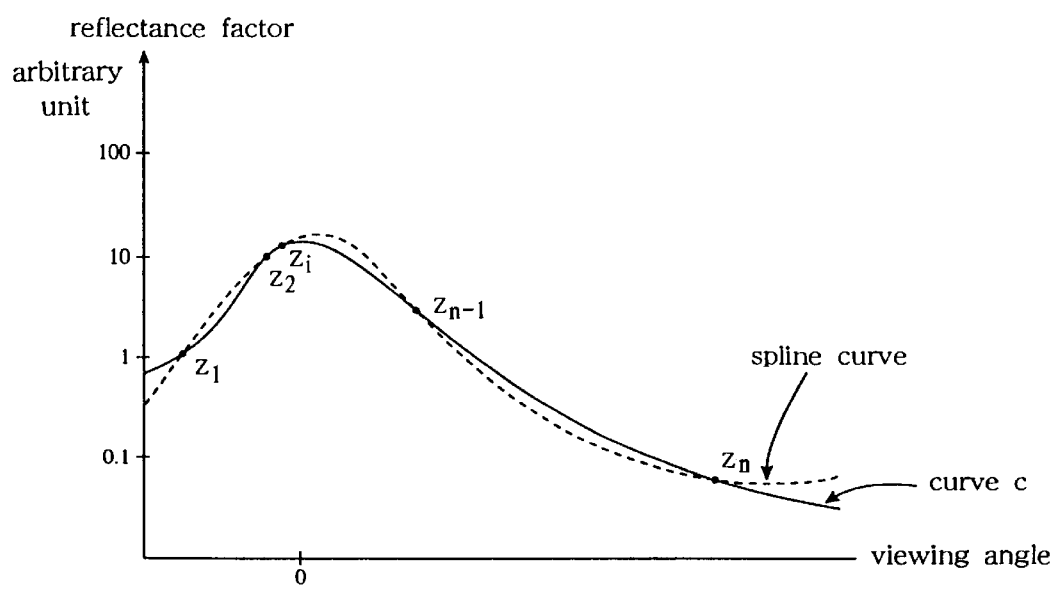
FIG. 3 is a graph showing a curve C of a reflectance factor of the specimen in a particular wavelength.

The light from the specimen surface is reflected toward all the directions in a space to which the direction of the incident light to the specimen surface belongs. When the specimen has a perfectly diffuse surface as shown by a in FIG. 2, the intensity of reflected light is uniformly equal in all the directions. On the other hand, when the specimen has the surface coated with a metallic or pearlescent coating such as a glossy coating, a pearlescent coating, the light is intensely reflected in a specular direction as shown by b in FIG. 2. In FIG. 3. a curve C represents a change with respect to the viewing direction in the reflectance factor of the specimen relative to a certain particular wavelength. The curve C can be determined in accordance with observed data by determining many points on the curve C.

However, there is no need to determine many points on the curve C in the portion where the curve C has a fixed curvature. In this portion having the fixed curvature, the determination of a few passing points is consequently enough. On the other hand, it is necessary to determine the points in more detail in the portion where the curve C has a greatly varying curvature.

An appropriate number of points can be specified on the curve C to specify a curve or a broken line whereby at least on these points said curve or said broken line coincide with the curve C, while other points it can locate near the curve C. One set of p points such as zag $Z_1, Z_2, \ldots, Z_i, \ldots, Z_p$ by which the curve or the broken line that can approximate the curve C with a predetermined appropriate accuracy are plotted on the curve C. Let us take the viewing angles (the tilt angle: 0) on these points as $\theta_1, \theta_2, \ldots, \theta_i, \ldots, \theta_p$.

Contrary to this. if the viewing angles (the tilt angle: 0) $\theta_1, \theta_2, \ldots, \theta_i, \ldots, \theta_p$ are specified relative to a predetermined wavelength. then the points $z_1, Z_2. \ldots, z_i, \ldots, z_p$ can be specified since the curve C is specified intrinsically relative to the coating surface and reflectance factor values of the points-can be determined by the observation. Accordingly, when one optional sequence of $\theta_1, \theta_2, \ldots, \theta_i, \ldots, \theta_p$ can be specified, one of the broken line or the curve passing through the respective point $z_i$ is determined. The values $\theta_1, \theta_2, \ldots, \theta_i, \ldots, \theta_p$ constituting a sequence $\Theta$ of p numerical values of angles may be any optional appropriate sequence, as far as they give the curve or the broken line approximating the curve C with a desired accuracy. For instance, the discovery of one sequence Θ can be considered to show a high possibility that the sequence of the numbers belonging to the neighborhood of the numbers in the discovered sequence can also ensure the predetermined accuracy. Accordingly, the innumerable sequences Θ in fact exist.

In the present invention, in order to discover any one of the sequences Θ, the sequences of p numerical values of angles are generated at random. This trial is repeated, until the curve or the broken line passing through these points can ensure a predetermined approximate accuracy relative to the curve C. This process can be performed by generating the uniform random numbers by the computer, as shown in FIG. 4. This detail is shown in FIG. 1.

Figure 1:
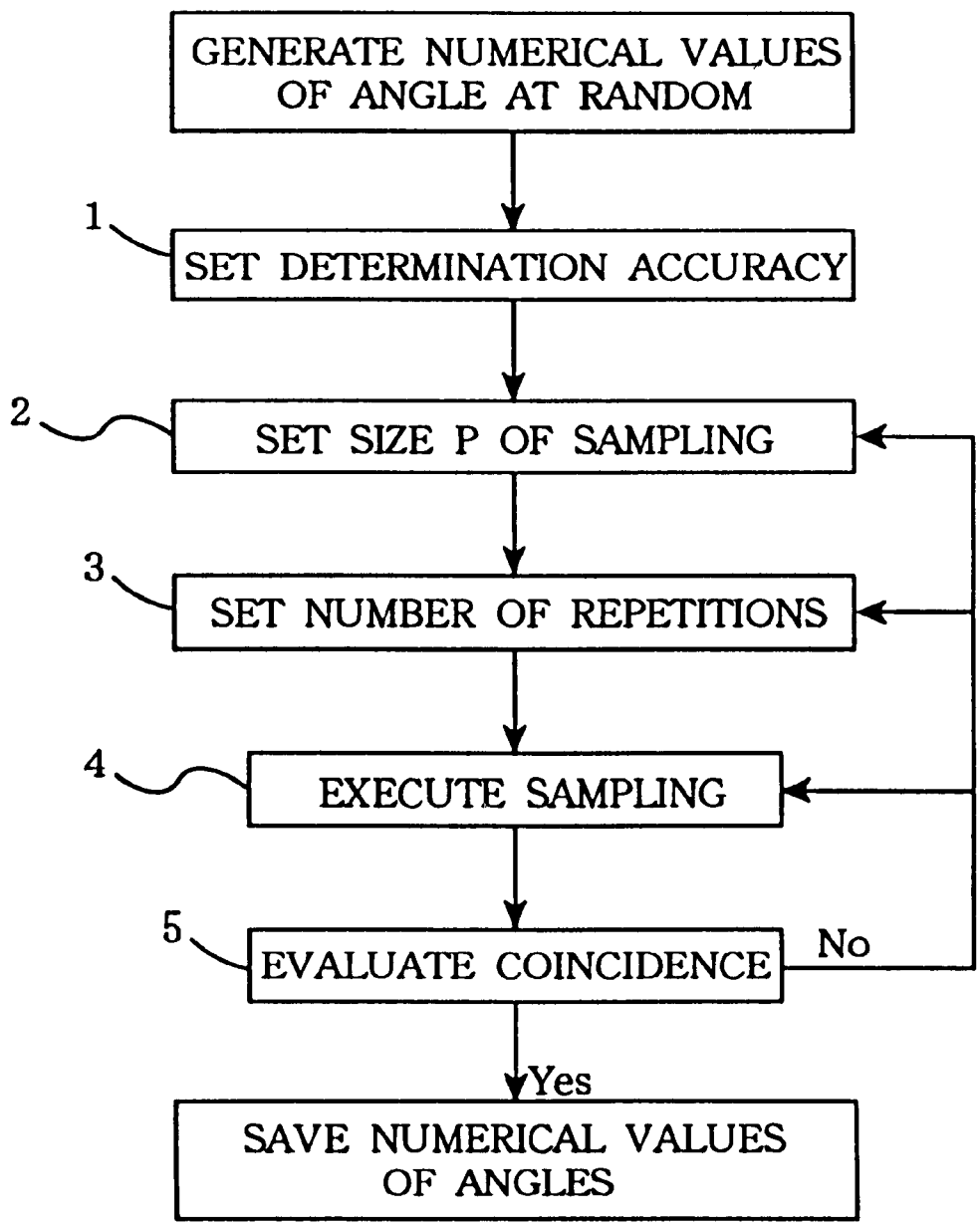
FIG. 1 is a block diagram showing a process for discovering any one of sequences $\Theta$.

In step 1 in FIG. 1, a desired accuracy is set. In step 2, the size p of random sampling is then set. In step 3, the number of sampling trials is set as needed. In step 4, the p-sized random sampling is performed. In step 5, the determination is made as to the extent of the coincidence between the curve C and the curve or the broken line passing through p points $Z_1, Z_2, \ldots, Z_i, \ldots, Z_p$ specified by p numerical values of angles obtained in step 4.

The present invention employs some means in order that a target sequence Θ can be determined by the random sampling with a fewer trials. One of the means is a spline curve using a three-order spline function or a Bezier curve. The spline function can calculate the spline curve smoothly passing through some points which are optionally set. Compared to a first-order or second-order spline function, the three-order spline function can obtain the much smoother spline curve and can improve the approximate accuracy. The Bezier curve is the smooth curve which is mathematically obtained by specifying the starting point and end point of the curve and further specifying the direction of extension of the curve on the specified points. According to this method, even any complicated curve can be described with a relatively small amount of data. Preferably, the specular direction is necessarily included in numerical values of sampling angles so that the curve C may necessarily coincide with the approximate curve at the spcular direction.

Figure 7:
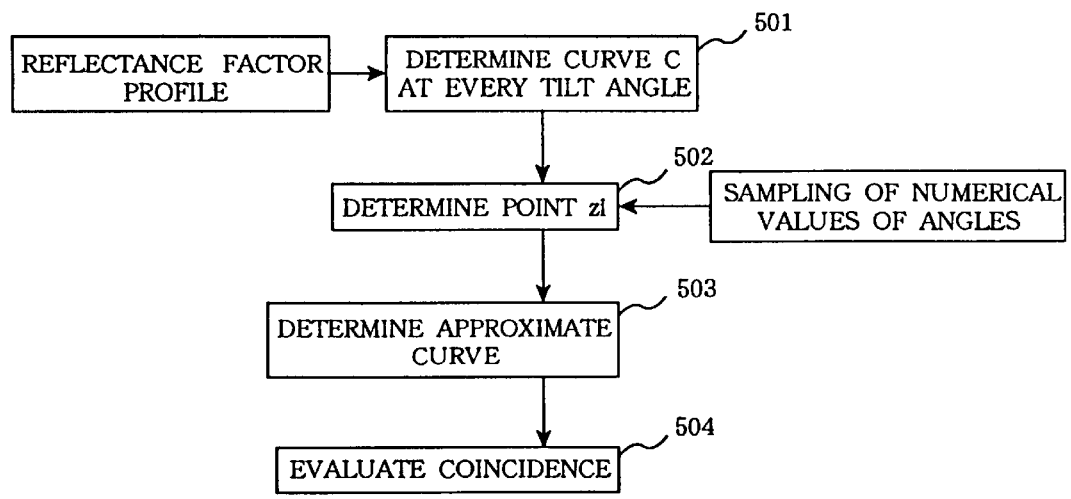
FIG. 7 is a block diagram describing in detail the execution of the above process.
Figure 6:
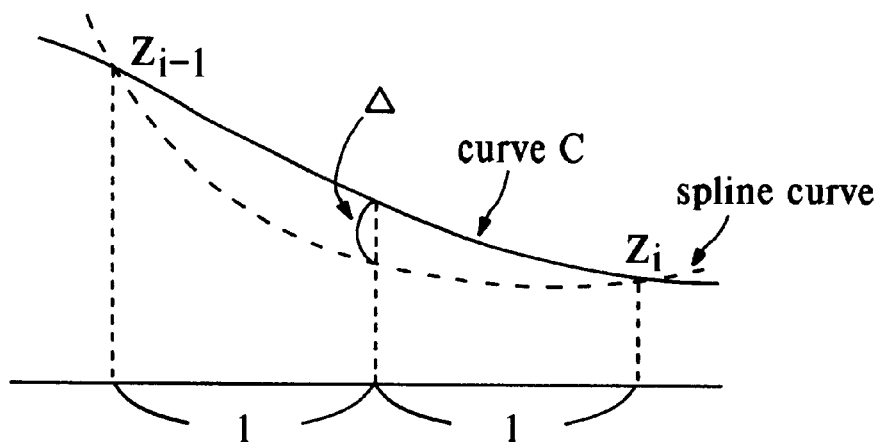
FIG. 6 illustrates how to determine a deviation from the curve C.

In step 5, whether the spline curve or the Bezier curve coincides with the curve C is determined. The execution of step 5 is shown in FIG. 7. The specimen coating plate to be the criterion previously undergoes a gonio-spectral colorimetry in about several thousands to about ten thousands viewing directions. Thereby, a reflectance factor profile is determined and in advance stored in a memory in the computer. In step 501, the curve C is in advance determined from this reflectance factor profile at each one or plural predetermined tilt angle(s). and this curve C is temporarily stored in the memory if needed. In step 502, p points. $z_1, z_2, \ldots, z_i, \ldots, z_p$ are specified on the curve C from the thus previously determined criterion curve C and the p numerical values of angles obtained in step 4. In step 503, the spline curve or the Bezier curve passing through the p points $z_1, Z_2, \ldots, z_i, \ldots, z_p$, namely, the predictive gonio-spectral reflectance factor distribution is determined. In step 504, whether the thus specified curve C coincides with the spline curve or the Bezier curve is determined. This determination can be made in the following manner. For example, as shown in FIG. 6, the square of a difference Δ between the curve C and the spline curve or the Bezier curve is first determined on the midpoint between the points $z_1$ and $z_2, \ldots$, the midpoint between the points $z_{i-1}$ and $z_i, \ldots$, the midpoint between the points $z_{p-1}$ and $z_p$. Then, whether or not the sum of the squares is a predetermined value or less is determined.

When the trial is made sufficiently many times, it will be possible to discover a plurality of sets of sequences Θ which can obtain the approximate curve within a predetermined accuracy. Meanwhile, when the sequences Θ capable of obtaining the approximate curve within a predetermined accuracy cannot be discovered within a predetermined number of trials, the sampling is again performed by increasing the number of trials or by increasing the size p of random sampling. The above steps are also performed for other tilt angles by optionally changing the tilt angle. Whether the sum n of all the thus obtained viewing directions is large or small can be appropriately specified depending on a desired accuracy. Preferably, n, i.e., the number of the viewing directions selected at random is in general 300 to 500.

In the present invention, at least one set of n capable of achieving the optional desired accuracy is thus selected and set as the fewer viewing directions than all the possible viewing directions.

In the present invention, the colorimetry is performed in n viewing directions selected by the appropriate method including any method described above. In this case, the wavelength of the colorimetry light can be appropriately selected. For example, about 35 to about 40 wavelengths may be set at random. This wavelength can in advance be put in the angle file or the measuring angle specification file as described above. Alternatively, an additional file for specifying the wavelength may be provided so as to describe the wavelength in this file.

Once n viewing directions are specified relative to a certain wavelength by the above method, the reflectance factor distribution can be reproducible regardless of the wavelength when it is unnecessary to take into account a refraction due to a coating film. Also, as far as a type of its metallic or pearlescent pigment is fixed, the reflectance factor distribution can be applicable regardless of the surface color of coating.

The possible viewing directions that can be measured by the goniospectrophotometer can be potentially directed toward infinitely all the points in the space to which the reflected light from the specimen surface directs, seen from the point of incidence. However, when the gonio-spectral reflectance factor distribution is determined relative to the actual object, viewing directions are generally set taking into account a limitation by a measuring mechanism of the device. Herein, the phrase "all the viewing directions that can be viewed by the goniospectrophotometer" covers all the directions that can be theoretically measured, however, in actual practice, it may be all the viewing directions that can be measured by the actual device.

In the present invention, preferably, all the directions that can be viewed by the goniospectrophotometer comprise: a plurality of viewing directions [1] in a plane of incidence consisting of viewing directions of each of steps in which a viewing angle is changed step by step by a predetermined increment angle in the plane of incidence, the plane of incidence being defined by an incident light emitted from a light source and a normal of a specimen surface, the viewing angle being defined as the angle formed between a reflection direction and a specular direction of the reflected light; and a plurality of viewing directions [2] consisting of viewing directions in each of the tilt planes of which a quasi-viewing angle is changed step by step by a predetermined increment angle in said tilt planes, said tilt planes being tilted by each tilt angle which is step by step changed by a predetermined increment angle relative to the specimen surface, the quasi-viewing angle being defined as the angle formed between a reflection direction and a quasi-specular direction of the reflected light, whereby in a region of angle where the viewing angle is a predetermined value or less, the viewing directions [1] are determined by setting the increment angle to a smaller value compared to the angle region where the viewing angle exceeds the predetermined value, and in a region of angle where the quasi-viewing angle is a predetermined value or less, the viewing directions [2] are determined by setting the increment angle to a smaller value compared to the angle region where the quasi-viewing angle exceeds the predetermined value.

The directions of all the points in the space can be also the objects to be random-sampled. In this case, the numerical values of angles obtained by sampling do not sometimes correspond to the angles measurable by the goniospectrophotometer. Thus, the trial of sampling may be performed until all the numerical values of angles obtain the values corresponding to the angles measurable by the goniospectrophotometer.

Preferably, the colorimetry in a plurality of viewing directions selected at random is performed by the steps: a step [A] of gathering colorimetry data of the reflected light in the plane of incidence in the corresponding viewing directions of the plurality of viewing directions selected at random while changing the viewing angle defined as the angle formed between the reflection direction and the specular direction of the reflected light in the plane of incidence; and a step [B] of gathering colorimetry data of the reflected light in at least one tilt plane tilted by a predetermined tilt angle relative to the specimen surface in the corresponding viewing directions of the plurality of viewing directions selected at random while changing the quasi-viewing angle defined as the angle formed between the reflection direction and the quasi-specular direction of the reflected light in the tilt plane.

Figure 9:
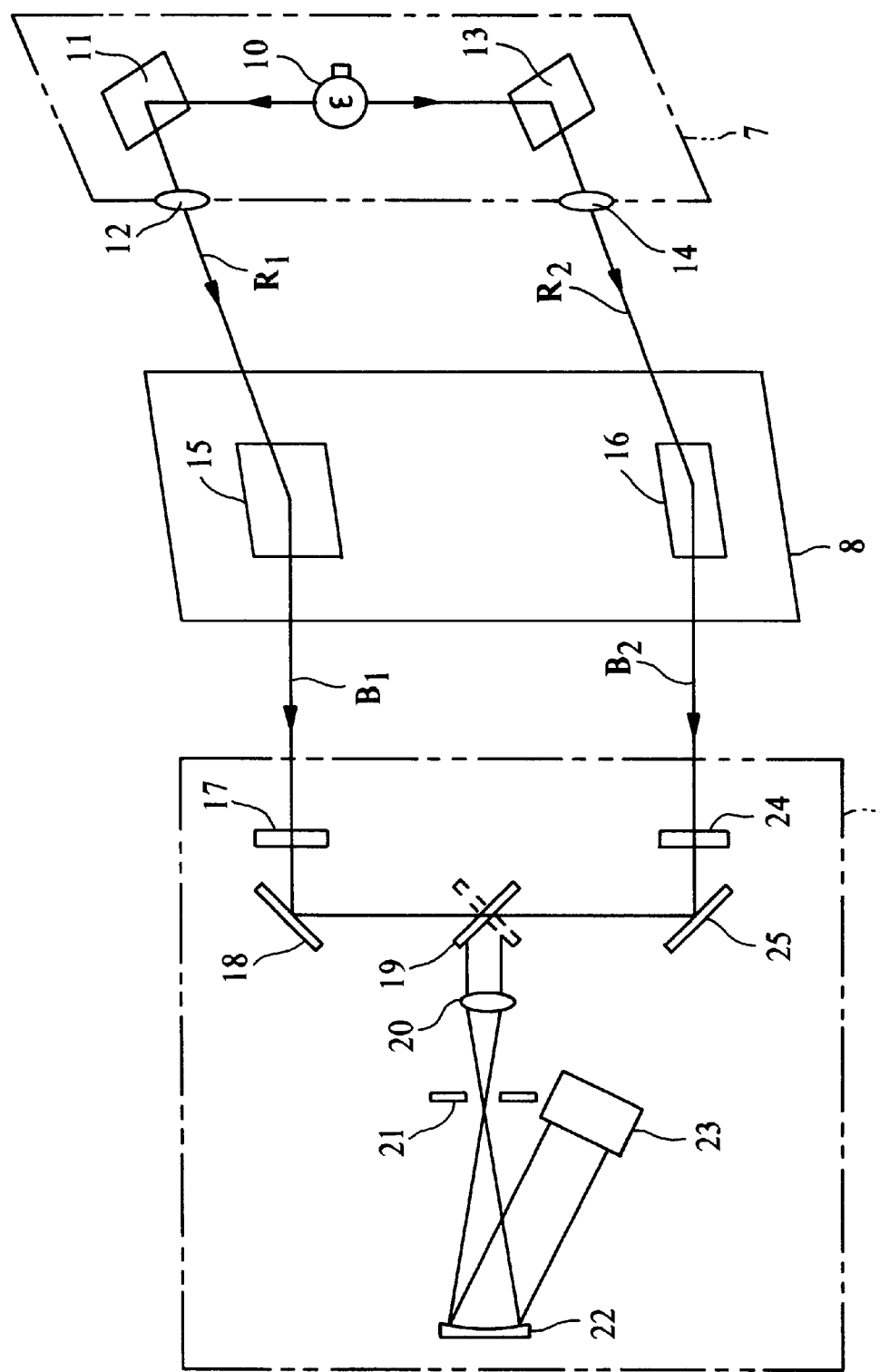
FIG. 9 shows a constitution of a goniospectrophotometer.

An exemplary constitution of the goniospectrophotometer is shown in FIG. 9. The goniospectrophotometer comprises an illuminator 7, a specimen rotating table 8 and a spectroscope 9. The illuminator 7 includes a halogen lamp 10. The illuminating light emitted from the halogen lamp 10 is partially guided to the specimen rotating table 8 through a first projection mirror 11 and a first projection lens 12 and illuminates a specimen 15 as a specimen illuminating light R1. In socalled directions of diffuse reflection, the illuminating light emitted from the halogen lamp 10 is partially guided to the specimen rotating table 8 through a second projection mirror 13 and a second projection lens 14 and illuminates a white diffuser 16 as a white diffuser illuminating light R2.

The specimen 15 and the white diffuser 16 are attached in place on the specimen rotating table 8. The specimen illuminating light R1 is reflected in a predetermined viewing direction, thereby resulting in a light B1 reflected from the specimen. The reflected light B1 is guided to the spectroscope 9. On the other hand, the white diffuser illuminating light R2 illuminating the white diffuser 16 is reflected in the predetermined viewing direction, thereby resulting in a light B2 reflected from the white diffuser. The reflected light B2 is also guided to the spectroscope 4. That is, this goniospectrophotometer is fixed in the direction of optical axes of the illuminating lights R1 and R2 and the direction of optical axes of the reflected light B1 and B2 with respect to the specimen 15 and the white diffuser 16. Of course, both the directions of optical axes can be optionally changed within a predetermined range as needed.

Figure 8:
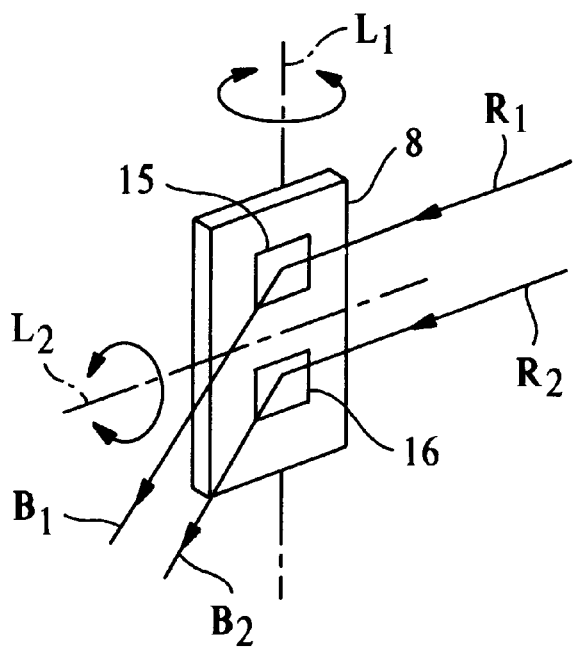
FIG. 8 shows a relationship between the angle of rotation of a specimen rotating table 3 around a vertical axis $L_1$ and the angle of rotation thereof around a horizontal axis $L_2$.

As shown in FIG. 8. the specimen rotating table 8 having the specimen 15 and the white diffuser 16 attached thereto can be rotated around a vertical axis $L_1$ and a horizontal axis $L_2$ by a drive mechanism (not shown). The specimen rotating table 8 is rotated around the vertical axis $L_1$, whereby the viewing angle defined as the angle formed between the viewing direction and the specular direction can be optionally changed in the specimen plane.

Also, the specimen rotating table 8 is rotated around the horizontal axis $L_2$, whereby the tilt angle can be optionally changed. The plane which is tilted by a tilt angle relative to the specimen plane is called the tilt plane. The specimen rotating table 8 is further rotated around the vertical axis $L_1$, whereby the quasi-viewing angle defined as the angle formed between the viewing direction and the quasi-specular direction can be optionally changed in the tilt plane. The quasi-specular direction means the direction which is moved onto the tilt plane by rotating the specular direction by the tilt angle, i.e., a straight line which is closest to a specular light in the tilt plane.

As shown in FIG. 9, the reflected light B1 from the specimen 15 is introduced into the spectroscope 9 and then guided to a sector 19 by a first light receiving mirror 18 through a first attenuator 17 if needed. The reflected light B1 passing through the sector 19 is guided to a diffraction grating 22 through a light receiving lens 20 and a slit 21. The spectrum of the light B1 is measured, and then the light B1 is photoelectrically converted by a photo-detector 23.

The reflected light B2 from the white diffuser 16 is guided to the sector 19 through a second attenuator 24 and a second light receiving mirror 25. Then, the reflected light B2 is photoelectrically converted in the same manner as the reflected light B1. In the case of the colorimetry in directions of specular reflection, the light from the light source is guided directly to the sector 19 instead of the reflected light B2. That is, a spectral colorimetry value of the light reflected from the specimen is expressed in the directions of diffuse reflection, by a relative value to the spectral colorimetry value of the light reflected from the white diffuser under the same condition, or, in the directions of specular reflection, by a ratio of an amount of received light to an amount of incident light under the same condition, i.e., by a specular reflectance factor.

As an example, a goniospectrophotometric color measurement system GCMS-4 (Murakami color research laboratory) or the like can be mentioned.

In the present invention, preferably, in the angle region where the viewing angle is a predetermined value or less, the viewing directions [1] are more highly densely sampled at random compared to the angle region where the viewing angle exceeds the predetermined value, and in the angle region where the quasi-viewing angle is a predetermined value or less, the viewing directions [2] are more highly densely sampled at random compared to the angle region where the quasi-viewing angle exceeds the predetermined value.

Preferably, the viewing directions of the goniospectrophotometer are controlled by the program stored in the computer.

The colorimetry data obtained by the present method reflects well the distribution of the data that can be obtained by the colorimetry in all the directions that can be measured by the goniospectrophotometer. However, the region where the function R is rapidly changed requires more data compared to other regions in order to determine the distribution. In the present invention, a Monte Carlo method is therefore used so as to perform an interpolation between the thus obtained data, if needed. This process will be described below.

The gonio-spectral reflectance factor R expressed as the multivariable function $R(\lambda, \theta_1, \theta_2, \theta_3, \theta_4)$ is generally difficult to analytically treat. The function R is actually defined as a collection of data composed of combinations of the gonio-spectral reflectance factors relative to these variables obtaind by performing very many measurements. And, if some points on the function R can be determined by the observation, a function value on an optional point between these points can be determined by the Monte Carlo method (e. g., "Handbook of numerical value calculation by FORTRAN", Ohmsha Ltd., 1990).

This function R may be expressed by the analytically treatable function in the limited region. It is assumed that the function $R(\lambda, \theta_1, \theta_2, \theta_3, \theta_4)$ can be expressed as equation (1):

$$R(\lambda, \theta_1, \theta_2, \theta_3, \theta_0) = R(x_1, x_2, x_3, x_4, x_5) = \Pi^5_{i=1}(b_i + c_i x_i) \quad (1)$$

where $b_i$, $c_i$ are appropriate constants, and $x_i$ is a variable resulting from a linear transformation of $\lambda$, $\theta_i$ into $[0, 1]$ in an appropriate interval. Herein, $\theta_1$, $\theta_2$, $\theta_3$ and $\theta_4$ are sometimes expressed together as $\theta_i$. When the function value in which $x_i$ corresponds to 0 or 1 is already known by the measurement, a function value $R(P)$ relative to an optional midpoint $P=(p_1, p_2, p_3, p_4, p_5)$, $0 \leq p_i \leq 1$ ($i=1, 2, 3, 4, 5$) is determined in the following manner. The above equation (1) can be expressed as equation (2):

$$R(x_1, \ldots, x_{j-1}, p_j, x_{j+1}, \ldots, x_5)$$
$$= (b_j + c_j p_j) \Pi'^5_{i=1}(b_i + c_i x_i)$$
$$= p_j R_1 + (1-p_j) R_0 \quad (2)$$

where $\Pi'$ is a product except $(b_j + c_j p_j)$, and $R_0$, $R_1$ are $R_a = R(x_1, \ldots, x_{j-1}, a, x_{j+1}, \ldots, x_5)$ ($a=0, 1$). Therefore, equation (3) can be expressed:

$$R(x_1, \ldots, x_{j-1}, p_j, x_{j+1}, \ldots, x_5)$$
$$= \Sigma r_j R(x_1, \ldots, x_{j-1}, \delta_j, x_{j-1}, \ldots, x_5) \quad (3)$$

where $\Sigma$ is subjected to $\delta_j=0, 1$ and $r_j$ is $1-p_j$ or $p_j$ by $\delta_j=0$ or 1. This procedure is repeated for other $p_i$, whereby equation (4) is generally expressed:

$$R(P) = \Sigma r_1 \cdot r_2 \cdot r_3 \cdot r_4 \cdot r_5 R(\delta_1, \delta_2, \delta_3, \delta_4, \delta_5) \quad (4)$$

Next, a random number $\alpha_1$ taking two values alone 0 and 1 (binomial distribution) is generated relative to $i=1, 2, 3, 4, 5$ by equation (5):

$$\alpha_i = 1 \text{(with probability } p_i\text{)}$$
$$= 0 \text{(with probability } 1-p_i\text{)} \quad (5)$$

The above equation (4) clearly represents an average value of variable R ($\alpha_1, \alpha_2, \alpha_3, \alpha_4, \alpha_5$). Therefore, the function value $R(P)$ for the optional point $P=(p_1, p_2, p_3, p_4, p_5)$ can be thus determined from an arithmetic average of the value R for plural $P=(\alpha_1, \alpha_2, \alpha_3, \alpha_4, \alpha_5)$. The probability (5) of random number generation is changed, thereby $R(P')$ for other optional point $P'=(p'_1, p'_2, p'_3, p'_4, p'_5)$ in the interval of said $\lambda$ and $\theta_i$, $0 \leq p_i' \leq 1$ ($i=1, 2, 3, 4, 5$) can be determined by the same approach.

The above process is repeated desired repetition, whereby the function value $R(P)$ for an optional number of points P can be determined by the Monte Carlo method. The thus determined interpolation value can be also used in addition to the colorimetry data.

The colorimetry data can be described and stored in an appropriate file format in a storage medium such as a flexible disk. One colorimetry database comprises a group of data composed of the spectral reflectance factors relative to some coating plates. A three-dimensional curved surface can be rendered by a three-dimensional computer graphics software in accordance with the gonio-spectral reflectance factor distribution which is read from this colorimetry database.

The present invention-will be described below in further detail with reference to examples, however the present invention is not limited to these examples.

MANUFACTURING EXAMPLE 1

Manufacturing of Metallic or Pearlescent Pigment Coating 800 parts by weight of solid content of acrylic resin (styrene/methyl methacrylate/ethyl methacrylate/hydroxyethyl methacrylate/methacrylate copolymer, number-average molecular weight of about 20000, hydroxide group value of 45, acid value of 15, solid content of 50%, solvent: xylene) and 20 parts by weight of solid content of melamine resin (Uvan 20SE (trade name) manufactured by Mitsui Toatsu Chemicals Inc., solid content: 60%) were mixed to thereby prepare vehicle resin for forming the coating film. Perrindo Maroon R-6436 as red pigments (perylene pigments manufactured by Bayer Ltd.) were pre-mixed in the vehicle resin and then dispersed by a sand grinder mill. Aluminum-flake pigments (average particle diameter: 20 $\mu$m) were then mixed at a blending ratio of perylene pigments to aluminum metal-flake pigments=100/200. These were uniformly mixed by a dispersion type agitator to thereby manufacture the metal-flake material coating.

EXAMPLE 1

The personal computer was used so as to generate at random the numerical values of angles in the angle file by the random number generating program, where one set of angles comprises the incident angle, the reflection angle and the tilt angle. One set of these three angles is described in one line in the angle file in accordance with the above-mentioned format. The minimum unit of the angle was expressed by the double-precision floating point. The numerical values of angles, which can be measured by the goniospectrophotometer (Murakami color research laboratory, GCMS-4), were transcribed into the measuring angle specification file from these numerical values of angles by selecting 350 viewing directions. The colorimetry wavelengths ware described within a range of 400–730 nm in this measuring angle specification file. A structure of the measuring angle specification file is as described below. For implementing the colorimetry, the order of description of the wavelengths and angles in the file was optimized in accordance with the measuring device used.

<The number of measured wavelengths><Line feed>
  <Wavelength 1>|<Wavelength 2>| . . . |<Wavelength m><Line feed>
  <Line feed>
  <Incident angle 1>|<Viewing angle 1>|<Tilt angle 1><Line feed>
  <Incident angle 2>|<Viewing angle 2>|<Tilt angle 2><Line feed>
  . . .
  <Incident angle n>|<viewing angle n>|<Tilt angle n><Line feed>
  <File end>

Making of Standard Specimen Coating Plate

Orga S-90 Sealer (Nippon Paint Co. Ltd.) was applied to a tinplate (0.3×100×200 mm) so that a dry film thickness may be 40 μm, and then it was baked at 140° C. for 30 minutes. This was covered with the coating manufactured in Manufacturing example 1 so that a base color may be hidden and the film thickness may be 19–20 μm. This was then covered with acrylic/melamine resin clear coating (Nippon Paint Co. Ltd., Superlac 0–100) with the film thickness of 39–40 μm to obtain the standard specimen coating plate for the colorimetry.

The standard specimen coating plate underwent the colorimetry by the use of the goniospectrophotometer (Murakami color research laboratory, GCMS-4) and the data was stored in a storage for making the colorimetry database. The colorimetry was accomplished by controlling the goniospectrophotometer by the computer by the use of the measuring angle specification file. The time required for the colorimetry was about 3 hours.

Formation of 3-D Computer Graphics Image

Figure 10:
FIG. 10 shows a three-dimensional computer graphics image of an automobile generated by example 1.

The obtained colorimetry database was used so as to form the three-dimensional computer graphics image of an automobile by the three-dimensional computer graphics software (Integra, Inc., PEARL). This is shown in FIG. 10.

EXAMPLE 2

Collection of Standard Colorimetry Data

The standard specimen coating plate obtained by Example 1 underwent the colorimetry at every 10 nm within the range of 400–730 nm by the use of the goniospectrophotometer (Murakami color research laboratory, GCMS-4). The incident angle was fixed to 45°, and the viewing direction was set in such a manner that the increment angle was taken as 0.5° in the region having the viewing angle of 10° or less and the increment angle was taken as 1.5 in the region having the viewing angle exceeding 10°. Then, 19 tilt angles (−30.1948, 26.37929, −10.30226, 26.973168, 36.49954, 54.20702, 1.875836, −0.024122, 49.21656, 4.493385, −22.32618, −68.40623, 1.56824, 7.76847, −51.72559, 69.29945, 22.37375, 21.77998, −39.89323) were selected and colorimetry was performed in the same manner. The time required for the measurement was about 80 hours. This data was stored in the storage in the computer.

Selention of Reviewing Directions

With the tilt angle of 0° the spline curve for one set of viewing angles comprising 15 numerical values of angles selected at random was determined by the three-order spline function by the use of the colorimetry value of the corresponding or most approximate viewing angle in the above measured data. The deviation between this spline curve and the distribution curve drawn-from the above measured data was determined as the sum of squares of displacement of the midpoint between two adjacent data points.

The above operation was repeated for each of 30 (thirty) sets of viewing angles, each set comprising 15 numerical values of angles selected at random. The sets having the smallest deviation in these sets (75.95186, −62.26967, 57.51838, 35.34726, 6.091624. −25.72676, −59.60946, 33.16944, 40.1842,25.46019, −15.03113, 47.80142, −63.45712, 10.44323, 50.33712) were selected as the viewing directions in the case of the tilt angle of 0°.

The same operation was repeated for other 19 tilt angles. The sets having the smallest deviation were selected as the viewing directions. The total 300 viewing directions were thus selected.

The data corresponding to the selected viewing directions was stored in the storage.

Formation of 3-D Computer Graphics Image

The obtained colorimetry database was used so as to form the three-dimensional computer graphics image of the automobile by the three-dimensional computer graphics software (Integra, Inc., PEARL). In visual observation, there was no substantial difference between this formed image and the image formed in Example 1.

Comparative Example 1

The colorimetry data itself of the standard specimen coating plate obtained in Example 2 was used so as to form the three-dimensional computer graphics image of the automobile in the same manner as Example 2. In this case, the viewing directions were not reduced to 300 directions, and all the measured data was used. This is shown in FIG. 11.

Figure 11:
FIG. 11 shows the three-dimensional computer graphics image of the automobile generated by comparative example 1.

The images of FIG. 10 and Example 2 have substantially the same image quality for practical use in texture expression as that of the image formed by using the colorimetry data of the conventional method of FIG. 11.

According to the present invention, the gonio-spectral reflectance factor database preferably available for the personal computer or the like can be created for the greatly reduced time compared to the conventional method and the highly-fine realistic three-dimensional computer graphics image can be formed by using the database.

What is claimed is:

1. A method of measuring a gonio-spectral reflectance factor for use in a database of colors of coating for forming a three-dimensional computer graphics image, wherein a light reflected from a measured specimen is subjected to a colorimetry in a plurality of viewing directions selected at random from all the directions that can be viewed by a goniospectrophotometer, said plurality of viewing directions being less than all the directions that can be viewed by the goniospectrophotometer.

2. The method according to claim 1, wherein as the method of selecting at random partial plural viewing directions from all the directions that can be viewed by the goniospectrophotometer. a plurality of sets of incident angles, viewing angles and tilt angles that can be measured by said goniospectrophotometer are selected at random to a predetermined number of sets from randomly generated numerical values of angles in an angle file in a computer.

3. The method according to claim 2, wherein said selected sets of the predetermined number of the measurable incident angles, viewing angles and tilt angles are described in a measuring angle specification file which is different from said angle file in a computer, and the angles in said measuring angle specification file are rearranged before starting the colorimetry.

4. The method according to claim 1, wherein as the method of selecting at random partial plural viewing directions from all the directions that can be viewed by the goniospectrophotometer, a gonio-spectral reflectance factor distribution of at least one coating plate to be a criterion is in advance determined, while a plurality of sets of numerical values of angles representing the viewing directions are generated at random, and a predictive gonio-spectral reflectance factor distribution is determined by the use of the reflectance factor specified by said gonio-spectral reflectance factor distribution in the viewing directions specified by said sets of numerical values of angles, whereby, when said predictive gonio-spectral reflectance factor distribution can be approximate to said original gonio-spectral reflectance factor distribution with a predetermined accuracy, then a plurality of viewing directions by which said predictive distribution can be determined are selected.

5. The method according to claim 4, wherein said predictive gonio-spectral reflectance factor distribution is determined by the use of a spline function or a Bezier curve.

6. The method according to claim 1, wherein all the directions that can be viewed by the goniospectrophotometer comprise:

a plurality of viewing directions [1] in a plane of incidence consisting of viewing directions of each of steps in which a viewing angle is changed step by step by a predetermined increment angle in said plane of incidence, said viewing angle being defined as the angle formed between a reflection direction and a specular direction of the reflected light; and a plurality of viewing directions [2] consisting of viewing directions in each of tilt planes of which a quasi-viewing angle is changed step by step by a predetermined increment angle in said tilt planes, said tilt planes being tilted by each tilt angle which is step by step changed by a predetermined increment angle relative to the specimen surface, said quasi-viewing angle being defined as the angle formed between a reflection direction and a quasi-specular direction of the reflected light, whereby in a region of angle where the viewing angle is a predetermined value or less, said viewing directions [1] are determined by setting the increment angle to a smaller value compared to the angle region where the viewing angle exceeds said predetermined value, and in a region of angle where the quasi-viewing angle is a predetermined value or less, said viewing directions [2] are determined by setting the increment angle to a smaller value compared to the angle region where the quasi-viewing angle exceeds said predetermined value.

7. The method according to claim 6, wherein the colorimetry in a plurality of viewing directions selected at random is performed by the steps:

a step [A] of gathering colorimetry data of the reflected light in the plane of incidence in the corresponding viewing directions of said plurality of viewing directions selected at random while changing the viewing angle in the plane of incidence; and a step [B] of gathering colorimetry data of the reflected light in at least one of tilt plane in the corresponding viewing directions of said plurality of viewing directions selected at random while changing the quasi-viewing angle in the tilt plane.

8. The method according to claim 7, wherein in the angle region where the viewing angle is a predetermined value or less, said viewing directions [1] are more highly densely selected compared to the angle region where the viewing angle exceeds said predetermined value, and in the angle region where the quasi-viewing angle is a predetermined value or less, said viewing directions [2] are more highly densely selected compared to the angle region where the quasi-viewing angle exceeds said predetermined value.

9. The method according to claim 7, wherein a Monte Carlo method is used so as to perform an interpolation between the colorimetry data measured in the selected viewing directions.

10. The method according to claim 1, wherein the colorimetry is performed in 300 to 500 viewing directions selected at random.

11. The method according to claim 1, wherein the viewing directions of the goniospectrophotometer are controlled by the use of a personal computer.

12. The method according to claim 11, wherein said personal computer has at least a function of controlling the direction of a receiving light device of the goniospectrophotometer and a function of generating random numbers.

* * * * *